(12) United States Patent
Schwammenthal et al.

(10) Patent No.: US 7,429,269 B2
(45) Date of Patent: *Sep. 30, 2008

(54) AORTIC PROSTHETIC DEVICES

(75) Inventors: Ehud Schwammenthal, Ra'anana (IL); Yossi Tuval, Netanya (IL); Raphael Benary, Tel Aviv (IL)

(73) Assignee: Ventor Technologies Ltd., Ra'Anana (IL)

( * ) Notice: Subject to any disclaimer, the term of this patent is extended or adjusted under 35 U.S.C. 154(b) by 130 days.

This patent is subject to a terminal disclaimer.

(21) Appl. No.: 10/563,384

(22) PCT Filed: Jul. 6, 2004

(86) PCT No.: PCT/IL2004/000601

§ 371 (c)(1),
(2), (4) Date: Apr. 20, 2006

(87) PCT Pub. No.: WO2005/002466

PCT Pub. Date: Jan. 13, 2005

(65) Prior Publication Data

US 2006/0259134 A1 Nov. 16, 2006

Related U.S. Application Data

(60) Provisional application No. 60/485,156, filed on Jul. 8, 2003.

(51) Int. Cl.
*A61F 2/24* (2006.01)

(52) U.S. Cl. .................... 623/2.14; 623/2.15; 623/2.19

(58) Field of Classification Search ................ 623/1.24,
623/1.25, 1.26, 2.12, 21.3, 21.4, 2.15, 2.16,
623/2.17, 2.18, 2.19, 2.13, 2.14
See application file for complete search history.

(56) References Cited

U.S. PATENT DOCUMENTS

| 4,078,268 A | 3/1978 | Possis |
| 4,491,986 A | 1/1985 | Gabbay |

(Continued)

FOREIGN PATENT DOCUMENTS

EP          1 469 797          11/2005

(Continued)

OTHER PUBLICATIONS

U.S. Appl. No. 60/530,781.

(Continued)

*Primary Examiner*—Thomas J Sweet
(74) *Attorney, Agent, or Firm*—Ladas and Parry LLP

(57) ABSTRACT

A prosthetic device is provided for treatment of an aortic valve, having a compressed state for transarterial delivery and being expandable to an expanded state for implantation. The device includes an expandable support implantable in the expanded state of the prosthetic device in an aortic annulus, and an inner envelope having an upstream portion that lines the inner surface of the support, and a downstream portion which, when the prosthetic device is in the expanded state, extends into an aorta and defines a diverging conical section having a diameter that gradually increases from an upstream end of the section to a downstream end of the section. The section is configured to produce, during systole, a non-turbulent blood flow into the aorta with pressure recovery at the downstream end of the section. Other embodiments are also described.

15 Claims, 11 Drawing Sheets

U.S. PATENT DOCUMENTS

| | | | |
|---|---|---|---|
| 4,759,958 | A | 7/1988 | Numata et al. |
| 4,846,830 | A | 7/1989 | Knoch et al. |
| 4,994,077 | A | 2/1991 | Dobben |
| 5,108,425 | A | 4/1992 | Hwang |
| 5,178,632 | A | 1/1993 | Hanson |
| 5,332,402 | A | 7/1994 | Teitelbaum |
| 5,344,442 | A | 9/1994 | Deac |
| 5,354,330 | A | 10/1994 | Hanson et al. |
| 5,411,552 | A | 5/1995 | Andersen et al. |
| 5,840,081 | A | 11/1998 | Andersen et al. |
| 5,855,601 | A | 1/1999 | Bessler et al. |
| 5,908,451 | A | 6/1999 | Yeo |
| 5,908,452 | A | 6/1999 | Bokros et al. |
| 5,957,949 | A | 9/1999 | Leonhardt |
| 5,964,405 | A | 10/1999 | Benary et al. |
| 6,076,742 | A | 6/2000 | Benary |
| 6,091,042 | A | 7/2000 | Benary |
| 6,168,614 | B1 | 1/2001 | Andersen et al. |
| 6,171,335 | B1 | 1/2001 | Wheatley et al. |
| 6,287,339 | B1 | 9/2001 | Vazquez et al. |
| 6,312,465 | B1 | 11/2001 | Griffin |
| 6,338,740 | B1 | 1/2002 | Carpentier |
| 6,425,916 | B1 | 7/2002 | Garrison et al. |
| 6,454,799 | B1 | 9/2002 | Schreck |
| 6,458,153 | B1 | 10/2002 | Bailey |
| 6,582,462 | B1 | 6/2003 | Andersen et al. |
| 6,652,578 | B2 | 11/2003 | Bailey et al. |
| 6,682,559 | B2 | 1/2004 | Myers |
| 6,730,118 | B2 * | 5/2004 | Spenser et al. ............. 623/1.24 |
| 6,761,736 | B1 | 7/2004 | Woo et al. |
| 6,767,362 | B2 | 7/2004 | Schreck |
| 6,790,229 | B1 * | 9/2004 | Berreklouw ................ 623/2.1 |
| 6,830,584 | B1 | 12/2004 | Seguin |
| 6,875,231 | B2 | 4/2005 | Anduiza et al. |
| 6,908,481 | B2 | 6/2005 | Cribier |
| 7,018,406 | B2 | 3/2006 | Seguin et al. |
| 7,018,408 | B2 | 3/2006 | Bailey |
| 7,137,184 | B2 | 11/2006 | Schreck |
| 7,147,663 | B1 | 12/2006 | Berg et al. |
| 7,198,646 | B2 | 4/2007 | Figulla et al. |
| 7,201,772 | B2 * | 4/2007 | Schwammenthal et al. 623/2.18 |
| 7,252,682 | B2 * | 8/2007 | Seguin ...................... 623/2.17 |
| 7,261,732 | B2 * | 8/2007 | Justino ...................... 623/1.24 |
| 2002/0026233 | A1 | 2/2002 | Shaknovich |
| 2002/0032481 | A1 * | 3/2002 | Gabbay ...................... 623/2.11 |
| 2002/0186558 | A1 | 12/2002 | Plank et al. |
| 2003/0023300 | A1 | 1/2003 | Bailey |
| 2003/0040792 | A1 * | 2/2003 | Gabbay ...................... 623/2.11 |
| 2003/0130727 | A1 | 7/2003 | Drasler |
| 2003/0130729 | A1 | 7/2003 | Paniagua et al. |
| 2003/0171805 | A1 | 9/2003 | Berg |
| 2003/0236568 | A1 * | 12/2003 | Hojeibane et al. .......... 623/1.24 |
| 2004/0044402 | A1 | 3/2004 | Jung |
| 2004/0059429 | A1 | 3/2004 | Amin et al. |
| 2004/0093070 | A1 * | 5/2004 | Hojeibane et al. .......... 623/1.15 |
| 2004/0106976 | A1 | 6/2004 | Bailey et al. |
| 2004/0186563 | A1 | 9/2004 | Lobbi |
| 2004/0210304 | A1 * | 10/2004 | Seguin et al. .............. 623/2.11 |
| 2004/0260389 | A1 | 12/2004 | Case |
| 2005/0075720 | A1 | 4/2005 | Nguyen et al. |
| 2005/0096734 | A1 | 5/2005 | Majercak |
| 2005/0137688 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0182483 | A1 | 8/2005 | Osborne |
| 2005/0197695 | A1 | 9/2005 | Stacchino et al. |
| 2005/0240200 | A1 | 10/2005 | Bergheim |
| 2006/0025855 | A1 | 2/2006 | Lashinski et al. |
| 2006/0025857 | A1 | 2/2006 | Bergheim et al. |
| 2006/0058872 | A1 | 3/2006 | Salahieh et al. |

FOREIGN PATENT DOCUMENTS

| | | |
|---|---|---|
| WO | WO 98/29057 | 7/1998 |
| WO | WO 2005/002466 | 1/2005 |

OTHER PUBLICATIONS

U.S. Appl. No. 60/465,141.

Heinrich RS et al., Ann Biomed Eng. Nov.-Dec. 1996;24(6):685-94. Experimental analysis of fluid mechanical energy losses in aortic valve stenosis: importance of pressure recovery.

Marcus RH et al., Circulation. Sep. 1, 1998;98(9):866-72. Assessment of small-diameter aortic mechanical prostheses: physiological relevance of the Doppler gradient, utility of flow augmentation, and limitations of orifice area estimation.

PD Stein et al., Circulation Research, vol. 39, 5 8-65, 1976 by American Heart Association. Turbulent blood flow in the ascending aorta of humans with normal and diseased aortic valves.

Weyman AB et al., Rev Cardiovasc Med. 2005;6(1)23-32 Aortic Stenosis: Physics and Physiology-What Do the Numbers Really Mean?

Deac RF et al., Ann Thorac Surg. Aug. 1995;60(2 Suppl):S433-8. New evolution in mitral physiology and surgery: mitral stentless pericardial valve.

Heinrich RS et al., J Heart Valve Dis. Sep. 1999;8(5):509-15. Valve orifice area alone is an insufficient index of aortic stenosis severity: effects of the proximal and distal geometry on transaortic energy loss. (an abstract).

* cited by examiner

AORTIC PROSTHETIC DEVICES

This application claims the benefit of U.S. Provisional Application No. 60/485,156 filed Jul. 8, 2003 and incorporates the same by reference.

FIELD AND BACKGROUND OF THE INVENTION

The present invention relates to implantable prosthetic devices. The invention is particularly useful in prosthetic devices implantable by transarterial delivery for the treatment of aortic stenosis in the aortic valve of a patient's heart, and the invention is therefore described below with respect to such application. It will be appreciated, however, that the invention could also be used for other treatments, e.g., for aortic regurgitation and other valvular lesions. The invention also relates to methods for implanting such prosthetic devices.

Aortic stenosis is the obstruction of outflow from the left ventricular chamber into the aorta caused by restricted opening of the aortic valve during cardiac contraction. The diminished aortic valve opening area (from normally 3 $cm^2$ to less than 0.5 $cm^2$ in severe cases) results in a significant pressure drop across the valve, and normal cardiac output and aortic pressure can only be maintained at the expense of an increased intraventricular pressure. The high pressure which has to be generated by the left ventricular chamber results in increased wall tension and myocardial oxygen demand. Adaptive processes such as hypertrophy (compensatory increase in muscle mass) allow the heart to withstand this increased pressure load for some time, but ultimately, pump failure is inevitable.

In the majority of cases (and in more than 90% of all patients older than 65 years) aortic stenosis is caused by progressive fibrous and calcified degeneration of an originally normal valve, a process which is favored by hyperlipoproteinemia, arterial hypertension, and aging (acquired calcified aortic stenosis). The average survival of a patient with severe aortic stenosis and shortness of breath is less than two years. Since death may occur suddenly in a substantial portion of cases, some investigators recommend preventive surgery even in asymptomatic patients, provided they are good surgical candidates.

Surgical results in the selected group of patients with isolated aortic stenosis are reasonable. Operative mortality in such patients is about 5%. However, most individuals with significant aortic stenosis are in their seventies and eighties. These patients have usually multiple comorbid risk factors, such as coronary artery disease, cerebrovascular disease, generalized atherosclerosis, renal failure, or diabetes. Consequently, surgical mortality and morbidity are substantial. Moreover, if the calcified aortic valve is replaced by a mechanical prosthesis, anticoagulation is mandatory to reduce thromboembolic complications, which exposes the patient to an increased risk of serious bleeding. Implantation of biological prostheses is usually preferred in the elderly, but surgically implanted biological valves may have a suboptimal hemodynamic profile, because the suture ring on which the valve needs to be mounted reduces the space available for the valve itself. This poses a particular problem in women, were bioprostheses of a smaller size (which have to be used because of the smaller cardiac dimensions) may result in significant residual outflow obstruction.

Because of the significant risk of elderly patients undergoing open-heart surgery on cardiopulmonary bypass, which includes death, disabling stroke, respiratory and renal complications, dilatation of the narrowed valve using balloon-catheters was hoped to provide an alternative to surgery. Unfortunately, because immediate results of the balloon dilatation are suboptimal, and recoil of the stenosis reoccurs within weeks and months in virtually all patients, outcome is as poor as in patients who do not undergo surgery. Balloon-dilatation is therefore considered only justified in patients with a clear contraindication to surgery or as a "bridging procedure".

Recently, in analogy to the use of stents in coronary arteries, it has been proposed to use valved stents in order to achieve a sufficiently large valve area and avoid elastic recoil and restenosis. Spencer et al (U.S. Pat. No. 6,730,118), Andersen et al (U.S. Pat. No. 5,840,081) and Gabbay (U.S. Pat. No. 4,759,758) all describe a valved stent of certain designs that are intended for transarterial deployment. Cribier et al describe, in WO 98/29057, a collapsible stent which has a valve attached to it by circumferential suturing. The mesh/valve system is deployed via an inflatable balloon. In 1992, Andersen et al. reported their experience with a foldable porcine aortic valve sutured in an expandable stainless-steel stent. The valved stent was mounted on an 18-22 mm balloon-catheter front-loaded in a 16F Mullins long sheath and implanted in the pulmonary position, completely displacing the pulmonary cusps (or leaflets), which were pressed between stent and pulmonary artery wall with full deployment of the stent. However, this approach could result in coronary artery occlusion when undertaken in the aortic position, which would be fatal to the patient.

Even when the stent is not deployed across the full area of the aortic annulus, atheromatous deposits on the ventricular side of the aortic cusps (or leaflets) may be pushed against the ostia of the coronary arteries causing severe coronary obstruction or embolization. Severe distention of a heavily calcified aortic valve to allow deployment of a sizeable stent may also cause embolization of calcium deposits from the valve or a tear in the valve resulting in significant aortic regurgitation. Furthermore, a large stent-valve may also interfere with surrounding structures such as the anterior mitral leaflet (causing damage to it or impairing its function), and if protruding into the left ventricular outflow tract, the basal ventricular septum, which is usually hypertrophied in significant aortic stenosis.

OBJECTS AND BRIEF SUMMARY OF THE PRESENT INVENTION

An object of the present invention is to provide another prosthetic device capable of transarterial delivery and particularly useful in the treatment of aortic stenosis. Another object of the invention is to provide a prosthetic device for implantation in an orifice formed in a wall of a body passageway and capable of delivery via the body passageway. Further objects of the invention are to provide methods for implantation of such prosthetic devices.

According to one aspect of the present invention, there is provided a prosthetic device for use in the treatment of aortic stenosis in the aortic valve of a patient's heart, the prosthetic device having a compressed state for transarterial delivery and being expandable to an expanded state for implantation, the prosthetic device comprising: an expandable metal base constructed so as to be implantable in the expanded state of the prosthetic device in the aortic annulus of the aortic valve; and an inner envelope lining the inner surface of the metal base; characterized in that the inner envelope in the expanded state of the prosthetic device extends into the aorta and is of a diverging conical configuration, in which its diameter gradually increases from its proximal end within the aortic annulus to its distal end extending into the aorta, such as to produce, during systole, a non-turbulent blood flow into the aorta with pressure recovery at the distal end of the plastic envelope.

The present invention thus recognizes that the maximum orifice area of an implantable aortic valve stent is necessarily confined by anatomical and pathological limitations and subsequent concerns about the safety of deployment. The present invention therefore aims to reduce a permanent loss of pressure across any given cross sectional flow area of the prosthetic device. This allows achieving a reasonable hemodynamic profile (low pressure gradients) even for relatively small-sized prosthetic devices, as well as optimizing the hemodynamic profile (reduce pressure gradients even further) for larger devices. The invention thus effects pressure-recovery by streamlining the outlet geometry in order to avoid the occurrence of turbulence and kinetic energy dissipation as in a Venturi-meter.

According to further features in the described preferred embodiments, in the expanded state of the prosthetic device, the inner envelope of diverging conical configuration has a proximal end of 5-20 mm in diameter and a distal end of 15-30 mm in diameter, and is of 15-45 mm in length. In addition, the proximal end of the inner envelope includes a short straight section of uniform diameter within the aortic annulus effective to avoid flow separation through the inner envelope. Preferably, the short straight section has a length of 2-10 mm.

The device may thus be provided in various sizes to accommodate different prosthetic sizes (e.g. 12 to 29 mm biological prostheses) so that patients of all possible height and body surface area can be treated.

According to another aspect of the present invention, there is provided a prosthetic device for implantation in an orifice formed in a wall of a body passageway, the prosthetic device having a compressed state for delivery via the body passageway to the implantation site, and being expandable to an expanded state for implantation in the orifice; the prosthetic device comprising: an expandable metal base configured so as to be receivable in the orifice; and two annular clamps carried by the metal base and engageable with the opposite faces of the wall in the expanded state of the metal base for clamping the metal base within the orifice. In the described preferred embodiments, each of the two annular clamps includes an annular array of fingers.

As will be described more particularly below, such a construction is particularly useful for implantation in the aortic annulus of a patient's heart since it reduces the possibility of obstructing or occluding the coronary arteries, e.g., as compared to a prosthetic device requiring substantial expansion of the aortic annulus.

As will also be described more particularly below, the prosthetic device could also include a prosthetic valve for implantation with the metal base; alternatively, a prosthetic valve could be transarterially delivered and deployed in a separate operation.

According to yet another aspect of the present invention, there is provided a method of implanting a prosthetic device as described above in an orifice formed in a wall of the body cavity, comprising: introducing the prosthetic device in its compressed state into a catheter having a sheath engageable with and compressing the two annular clamps; delivering the catheter and prosthetic device via the body passageway to the implantation site, with the metal base located within the orifice, and the two annular clamps located on opposite sides of the wall formed with the orifice; moving the sheath to one side to release for expansion one of the annular clamps, and then the other of the annular clamps; and removing the catheter with the sheath from the body passageway, leaving the metal base implanted in the orifice with the annular clamps engaging the opposite sides of the wall.

According to a further aspect of the present invention, there is provided another method of implanting a prosthetic device as described above in an orifice formed in a wall of a body cavity, comprising: introducing the prosthetic device in its compressed state into a catheter having a first sheath engageable with one of the annular clamps for retaining it in the compressed state, and a second sheath engageable with the other of the annular clamps for retaining it in the compressed state; delivering the catheter and prosthetic device via the body passageway to the implantation site with the metal base located within the orifice, and the two annular clamps located on opposite sides of the wall in which the orifice is formed; moving the first sheath to one side to release the one annular clamp to its expanded state; moving the second sheath to the opposite side to release the second annular clamp to its expanded state; and removing the catheter and the sheathes from the body passageway, leaving the metal base implanted in the orifice with the annular clamps engaging the opposite sides of the wall.

It is will thus be seen that, in both methods, the device is implanted by the annular clamps engaging the opposite faces of the wall in which the device is implanted. In both cases, some expansion of the metal base may also be effected, but to a far lesser degree than the balloon-implanted devices of the prior art, which prior art devices increase the danger of obstructing or occluding coronary arteries. Nevertheless, according to a further feature in the described preferred embodiments, the prosthetic device of the present invention is preferably delivered via a balloon catheter so as to slightly expand the metal base sufficient to firmly engage the surface of the aortic annulus but not to the extent of deforming it such as to increase the risk of obstructing or occluding the coronary arteries.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS OF THE INVENTION

Figure 1A:
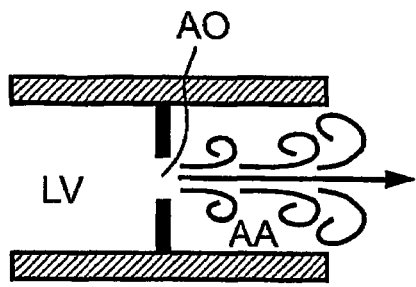
FIGS. 1a, 1b and 1c are diagrams helpful in explaining the health problem caused by a stenotic valve and the advantages of replacing a stenotic valve orifice by a prosthetic device constructed in accordance with the present invention.
Figure 1B:
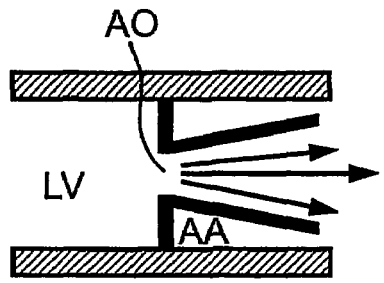
Figure 1C:
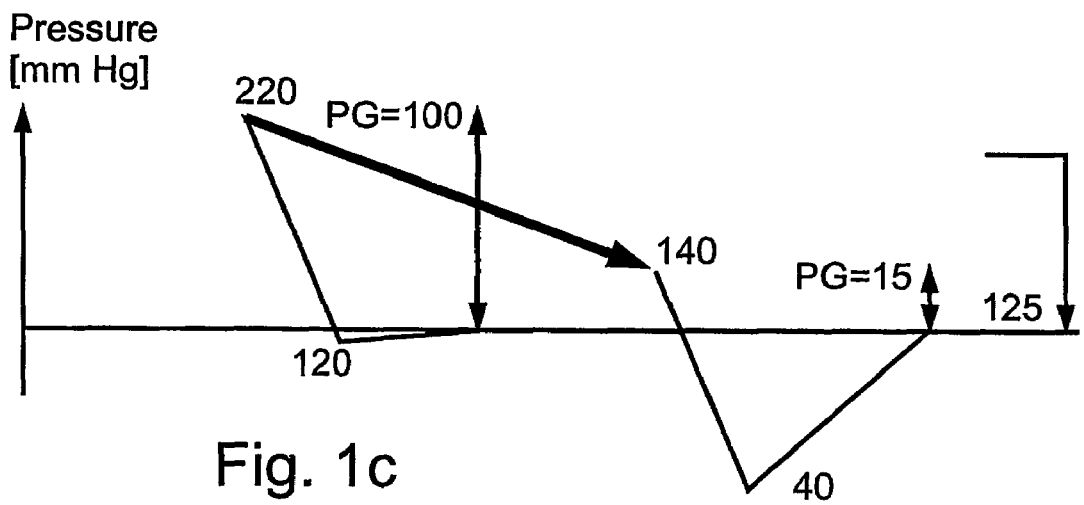
Figure 2:
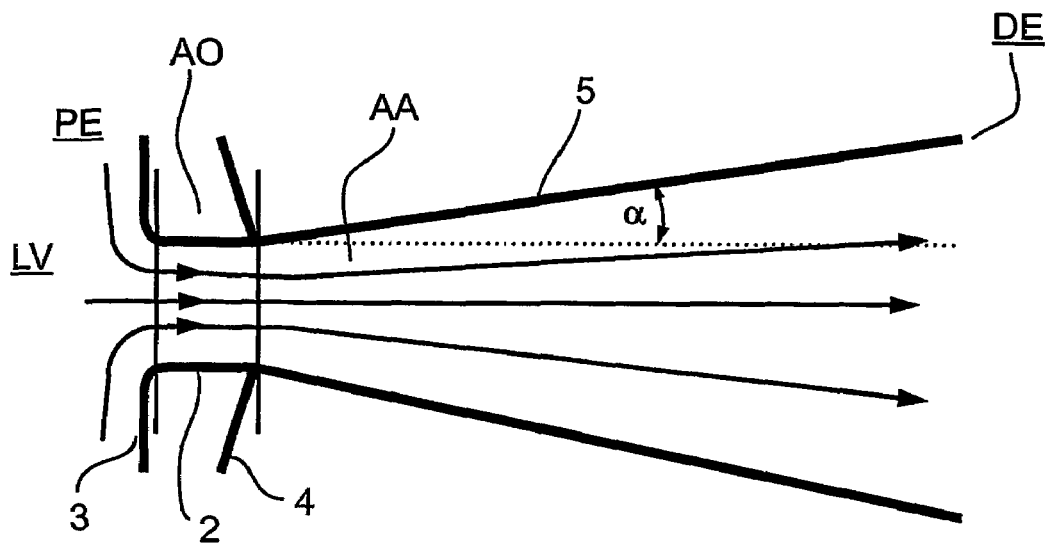
FIG. 2 is a diagram illustrating a prosthetic device constructed in accordance with the present invention to treat the above health problem by producing non-turbulent blood flow into the aorta with pressure recovery at the distal end of the prosthetic device.
Figure 3:
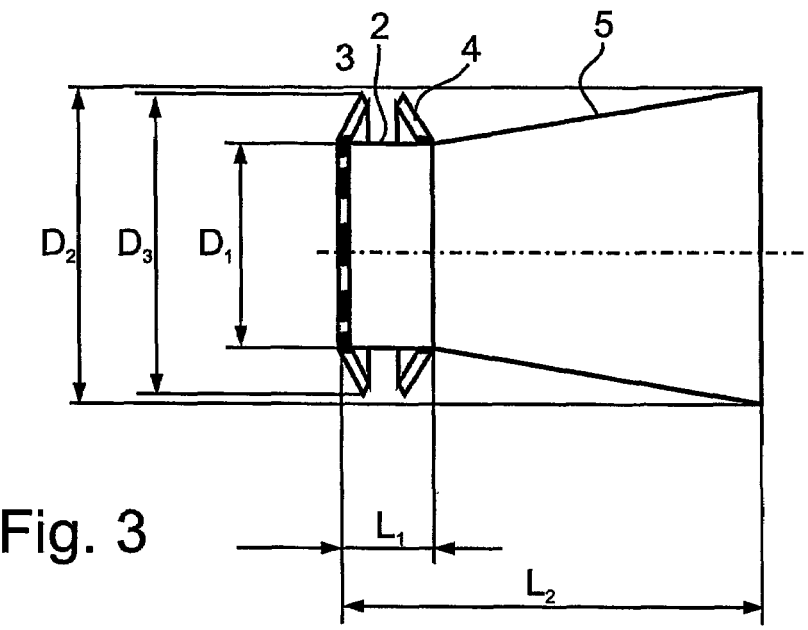
FIG. 3 is a side view of a prosthetic device constructed in accordance with FIG. 2.
Figure 4:
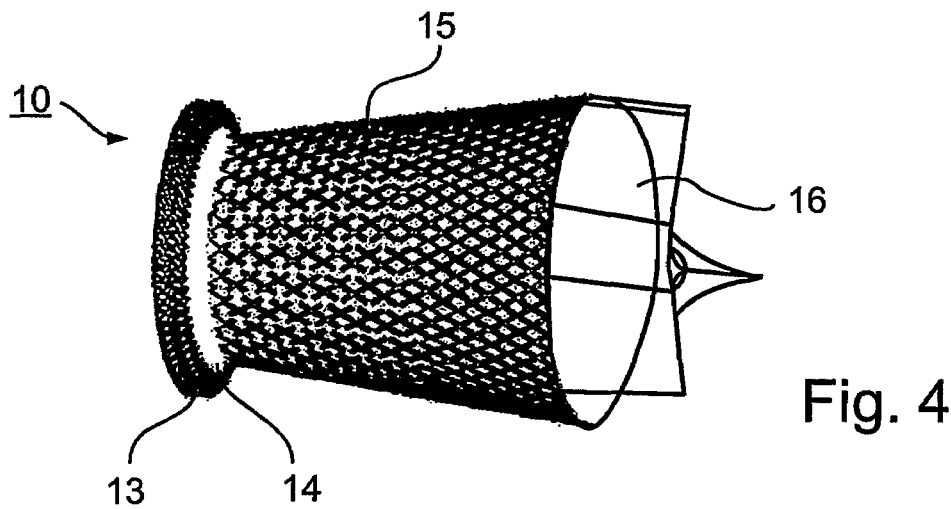
FIG. 4 is a three-dimensional view more particularly illustrating a preferred construction of the prosthetic device in accordance with the present invention.

Basic Concepts Involved (FIGS. 1-3)

As noted above, the present invention is primarily directed to implanting a prosthetic device into a diseased aortic valve for use in the treatment of aortic stenosis. This device is designed to aid blood pressure recovery so as to decrease the pressure gradient between the left ventricle and the aorta, thus alleviating the work load placed on the heart. FIG. 2 diagrammatically illustrates one construction of prosthetic device in accordance with the present invention, and FIGS. 1a-1c diagrammatically illustrate the manner in which such a prosthetic device may be used for alleviating the work load placed on the heart by an aortic valve suffering from significant aortic stenosis.

The principles of flow regulation in the cardiovascular system are quite similar to those in pipeline systems. Aortic pressure and cardiac output are regulated by the baroreceptor-system with its stretch-receptors in the aorta and carotid artery. Any loss of pressure will lead to a centrally mediated increase in cardiac output until the preset systemic pressure is again reached.

FIG. 1a thus diagrammatically illustrates how the blood flow, from the left ventricular LV through the aortic orifice AO into the aorta artery AA, is affected by a stenotic condition in the aortic orifice AO. Thus, such a stenotic condition effectively reduces the size of the aortic orifice AO to produce a turbulent flow into the aortic artery AA, which produces a substantial loss in pressure of the blood entering the aortic artery. Such pressure loss is sensed by the baroreceptor system which acts to increase the intraventricular pressure, thereby producing increased wall tension in the ventricular chamber, increased myocardial oxygen demand, and ultimately heart failure.

As shown in FIG. 1b, when a stenotic valve orifice, as shown in FIG. 1a, is replaced by a prosthetic device of the same throat size but including a Venturi tube configuration, namely one having a diverging conical configuration, there is produced a non-turbulent blood flow into the aorta with pressure recovery at the distal (wide) end of the device. The baroreceptor system will therefore not sense a loss of pressure, and will therefore not increase the left ventricular workload in order to compensate for such pressure loss. Accordingly, the replacement of a stenotic valve as shown in FIG. 1a, by a prosthetic device with a diverging conical configuration as shown in FIG. 1b, will reduce the workload placed on the left ventricular.

FIG. 1c diagrammatically illustrates the difference in the heart load when acting against a stenotic valve as shown in FIG. 1a, and when such a valve is replaced by a prosthetic device having the diverging conical configuration as shown in FIG. 1b. For purposes of example, the diagram of FIG. 1c is based on the following conditions: cardiac output is 5 l/min: the cross-sectional area of the throat is 0.5 $cm^2$; the required pressure gradient is 100 mm:Hg; and the aortic pressure demanded by the baroreceptors-system in the given example is 125. Thus, the substantial decrease in pressure head loss produced in the stenotic valve (FIG. 1a) will cause the blood pressure in the left ventricle to be 220 mm Hg in systole. However, the addition of a prosthetic device with the same critical area having the diverging conical configuration of FIG. 1b will provide a pressure recovery of 65 mm Hg, and will produce a blood pressure of 140 mm Hg in systole. In essence, pressure head loss is reduced from 95 o 15 mm Hg.

The prosthetic device diagrammatically illustrated in FIG. 2 includes an annular metal base 2 having a circular cross-section to be implanted in the aortic orifice AO; an annular clamp 3 at its outer end engageable with one face of the valve leaflets (cusps) in the aortic annulus; and another annular clamp 4 engageable with the opposite face of the valve leaflets. The base distal section 2 of the prosthetic device is relatively short, straight, of uniform diameter, and is located within the aortic orifice. The remainder of the prosthetic device extends into the aorta artery AA and is of a diverging conical configuration, as shown at 5, in which its diameter gradually increases from its proximal end PE within the heart left ventricle, to its distal end DE within the aorta. The angle of the taper ($\alpha$) of the diverging conical section 5 is determined according to dynamic fluid principles of Venturi flow, such as to produce a non-turbulent blood flow into the aorta, with pressure recovery at the distal end of the prosthetic device.

Thus, as well known in fluid dynamics relative to Venturi flow, the small-diameter of the base or throat section 2, increases the flow rate therethrough, thereby decreasing the static or lateral pressure; whereas the gradual expansion of the diverging conical section 5 decreases the flow rate, and thereby increases the static or lateral pressure. Such a construction produces a laminar or non-turbulent flow, reducing or eliminating flow separation in the diverging conical section 5, and thereby decreases head losses at the distal end DE of the prosthetic device.

As will be described more particularly below, the prosthetic device preferably carries a prosthetic valve at its distal end DE. Several commercial prosthetic aortic valve systems are currently available, generally classified as mechanical heart valves and biological heart valves, respectively.

In order to accommodate patients of different sizes and weights, the prosthetic device, in its expanded state, preferably should have the following dimensions as shown in FIG. 3: the diameter $D_1$ at the proximal end PE should be 5-20 mm; the diameter $D_2$ at the distal end DE should be 15-30 mm; the axial length $L_1$ from the proximal end to the distal end should be 15-45 mm; and the axial length of $L_2$ of the base or throat section 2 should be 2-10 mm.

A typical diameter $D_1$ of the throat section 2 will be 13 mm (covering only ⅔ of the average outflow tract diameter of an adult); a typical length $L_2$ will be 5 mm; a typical length ($L_1$, $L_2$) of the diverging conical section 5 will be 18 to 20 mm; and a typical angle α (widening angle, deviation from straight segment) will be from 12° to 25°, since an angle α of 12° produces almost full pressure recovery for laminar flow. For example, if the straight throat section 2 has a diameter of 13 mm (cross-sectional area 140 mm²), then a tube attached to this segment and widening with an angle α of 17° over a distance of 20 mm will have a diameter of 25 mm at its end (cross-sectional area 490 mm²). Consequently, this device will be able to accommodate a 25 mm biological prosthesis at its end (in the aorta) with favorable hemodynamic properties, although the throat size (straight segment within the valve) is only 13 mm in diameter.

The Prosthetic Device of FIGS. 4-8

As indicated earlier, a prosthetic device constructed in accordance with the present invention preferably also includes at the distal end DE of the diverging conical section 5, a prosthetic valve to be implanted with the prosthetic device. It is anticipated, however, that for some applications the prosthetic device may be implanted without a prosthetic valve, and the prosthetic valve implanted in a second subsequent operation in the aorta downstream of the prosthetic device.

FIGS. 4-8 illustrate a preferred prosthetic device construction including a prosthetic valve.

Figure 5:
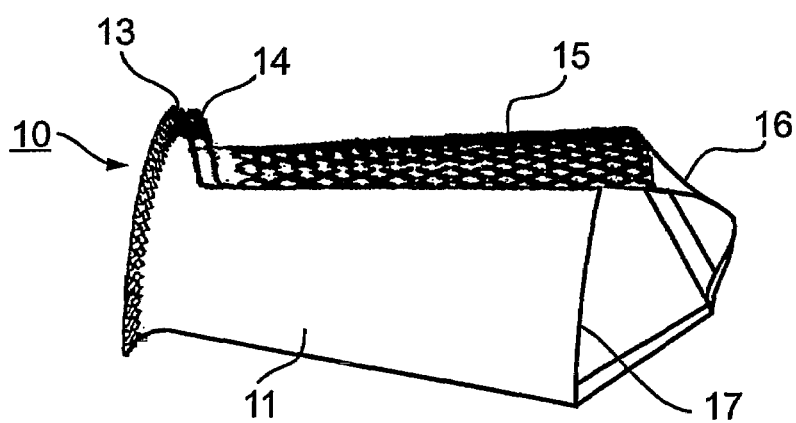
FIG. 5 a side view of the prosthetic device of FIG. 4.

Thus, as shown particularly in the sectional view of FIG. 5, the illustrated prosthetic device includes an expandable metal base 10 (e.g., of a mesh construction) so as to be transarterially deliverable via a catheter to the implantation site, in this case, the aortic annulus or orifice of an aortic valve affected by aortic stenosis. The illustrated prosthetic device further includes an inner envelope 11, e.g., of a flexible polymeric or other biocompatible material, lining the complete inner surface of metal base 10.

Metal base and its liner 11 of the illustrated prosthetic device include a short, straight throat section 12 constructed so as to be implanted in the aortic orifice (AO, FIG. 2). The prosthetic device further includes: an annular clamp 13 to engage the face of the valve leaflets (cusps) on one side of the aortic orifice; an annular clamp 14 to engage the face of the valve leaflets on the opposite side of the aortic orifice; and a diverging conical section 15 extending into the aorta artery AA. The construction is such that the diverging conical section 15 gradually increases in diameter from the short throat section 12 at the proximal end PE of the prosthetic device to its distal end DE, in order to produce a non-turbulent blood flow through the prosthetic device into the aorta, with pressure recover at the distal end, as described above with respect to the diagrams of FIGS. 1a-1c and 2.

The distal end of the illustrated prosthetic device carries a prosthetic valve 16. Preferably, prosthetic valve 16 is a collapsible mechanical or biological valve made of a pliable polymeric film which is effective to open the distal end of the prosthetic device during systole, and to close it during diastole. For example, prosthetic valve 16 may be made of the same material as liner 11 and attached thereto along a line of attachment, as shown at 17 in FIG. 5.

While a collapsible biological prosthetic valve is preferred, other prosthetic valves systems could be used, such as a ball-cage, a disc-cage, a tilting disc, a bileaflet, a check-valve, etc. It is also contemplated that a mechanical or synthetic prosthetic valve could be used.

Figure 6:
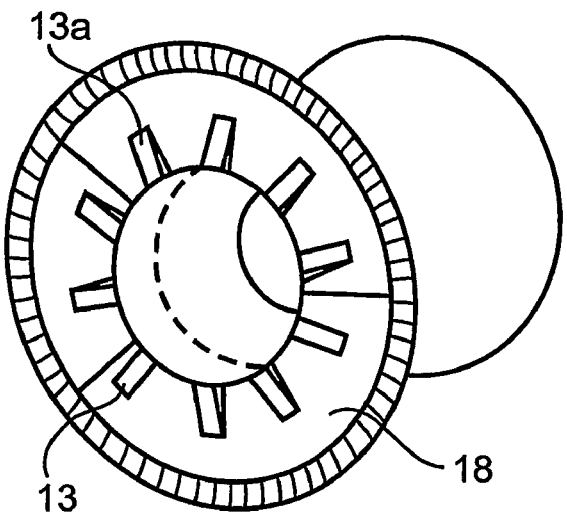
FIG. 6 is an end view from the heart side illustrating the prosthetic device of FIGS. 4 and 5 implanted in the aortic annulus.
Figure 7:
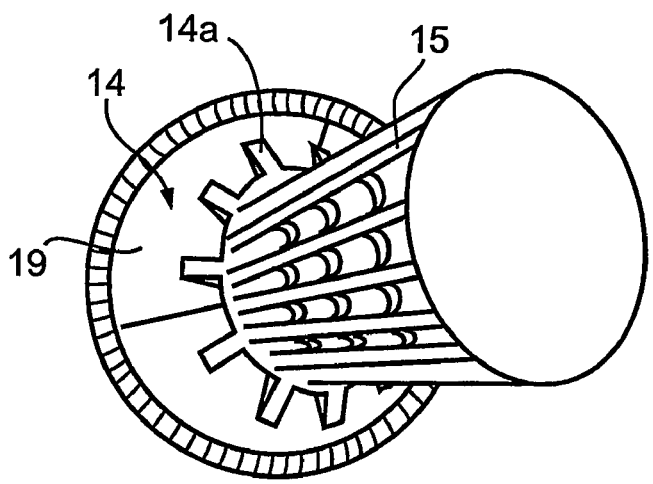
FIG. 7 is a perspective view from the aorta side of the implanted prosthetic device of FIGS. 4 and 5.
Figure 8:
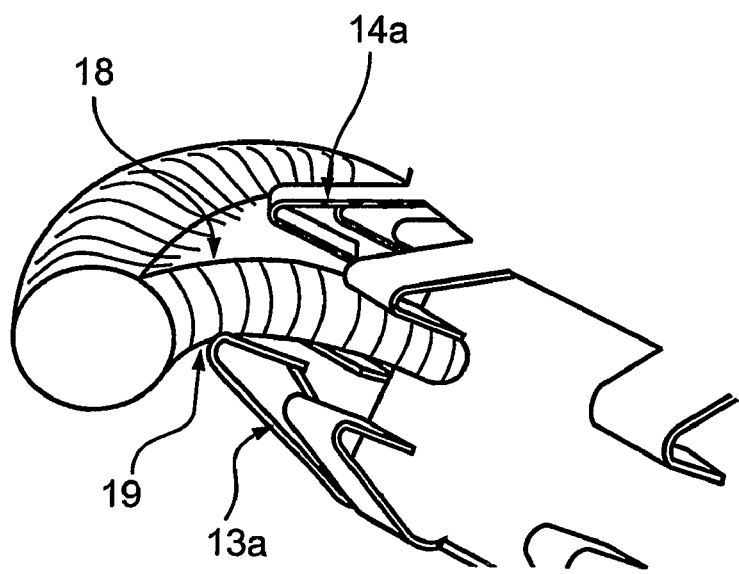
FIG. 8 is a fragmentary detail illustrating the manner in which the annular clamps engage the opposite sides of the valve leaflets in the implanted condition of the prosthetic device.

In the expanded condition of the illustrated prosthetic device, each of the annular clamps 13, 14 is constituted of an annular array of fingers which engage the surfaces of the valve leaflets (cusps) on the opposite sides of the aortic annulus, as illustrated more particularly in FIGS. 6-8. Thus, as illustrated particularly FIG. 8, annular clamp 13 includes an annular array of fingers 13a engageable with surface 18 (FIG. 6) of the native valve leaflets at the heart left-ventricle side of the aortic annulus AO; and annular clamp 14 includes a similar annular array of fingers 14a engageable with surface 19 (FIG. 7) of the native valve leaflets at the aorta side of the aortic annulus.

Any suitable method may be used for attaching the inner envelope or liner 11 to the inner surface of the metal base 15. For example, this may be done: by adhesive bonding, using a long-lasting biocompatible adhesive; by ultrasonic welding, using sonic energy to soften the plastic envelope 11 where it contacts the metal base; or by injection-molding the polymeric material to embed the metal base therein. Other possible methods include a mechanical locking arrangement wherein the inner envelope is mechanically locked to the metal base, or a suturing technique wherein the inner envelope is sutured to the metal base.

As broadly described above and as to be more particularly described below, the prosthetic device 10 is constructed to have a compressed state for transarterial delivery, and to be expandable to an expanded state for implantation. For this purpose, the metal base 10, including its diverging conical section 15 and its annualar clamps 13 and 14, may be of a pure metal, a metal alloy, or a combination thereof. Liner 11 may be of a suitable biocompatible polymeric or plastic material.

Examples of pure metals that may be used are tungsten, platinum, and titanium. Metal alloys possessing the required physical properties include (but are not limited to) Stainless Steel 316 and Nitinol (nickel titanium), both of which are biocompatible and commercially available. For example Nitinol may be used for the annular clamps 13 and 14, and the diverging conical section 5, while another conventional metallic stent material, such as Stainless Steel 316, may be used for the base or throat section 12. Dacron is typically used for covering nitinol-based devices, but other suitable biocompatible polymeric or elastomeric materials can be used for the inner envelope or liner 11.

Figure 9:
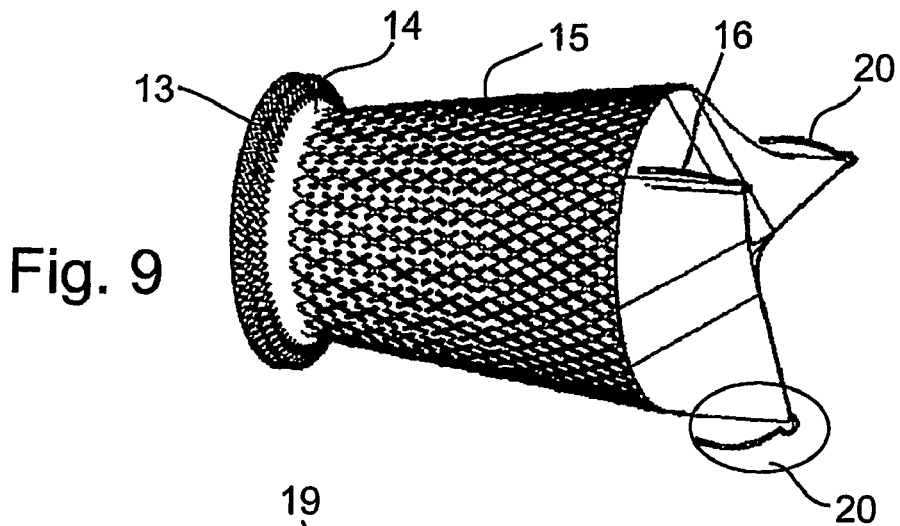
FIG. 9 illustrates a prosthetic device similar to that of FIG. 3 but including braces for bracing the distal end of the prosthetic device when implanted.
Figure 10:
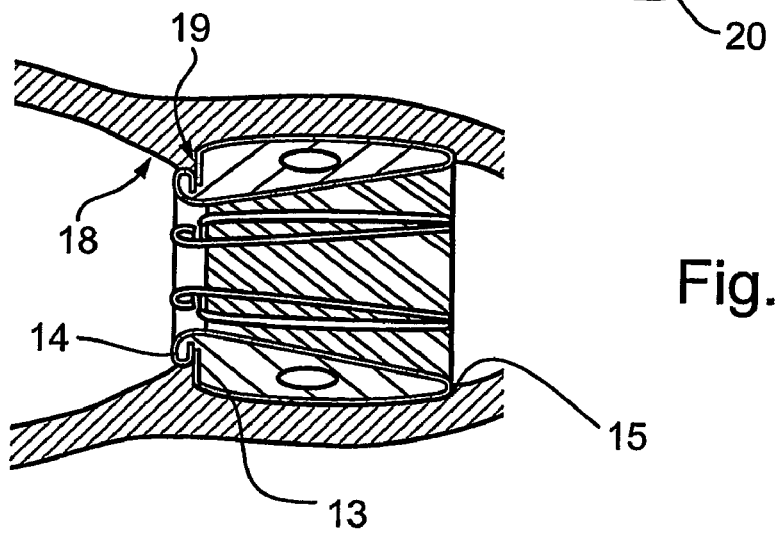
FIG. 10 illustrates the prosthetic device of FIG. 9 when implanted in the aortic annulus.
Figure 11:
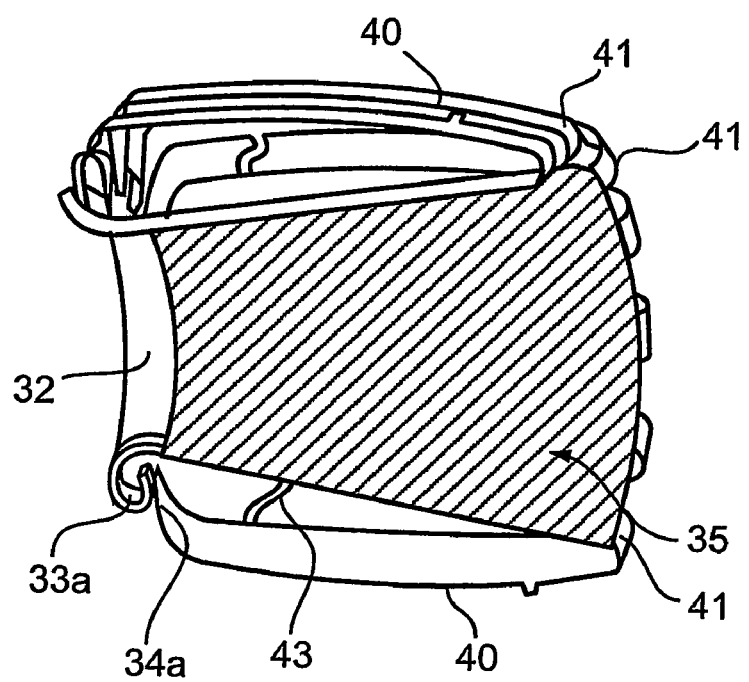
FIG. 11 illustrates another construction of prosthetic device in accordance with the present invention.

The Prosthetic Devices of FIGS. 9, 10 and FIG. 11

FIG. 9 illustrates a prosthetic device similar to that described above with respect to FIGS. 4-8, and therefore to facilitate understanding, corresponding parts have been identified by the same reference numerals. The main difference in the prosthetic device illustrated in FIG. 9 is the provision of a plurality of bracing elements 20 carried by the distal end DE of the metal base 10 and engageable with the inner surface of the aorta for bracing the prosthetic device, particularly its distal end, within the aorta as shown in FIG. 10.

FIG. 11 illustrates a modification wherein the bracing elements are integrally formed with the metal base, generally designated 30, particularly the clamping fingers 34a of the annular clamp 34 engageable with the distal (aorta) side of the valve leaflets in the aortic annulus. Thus, the bracing elements, generally designated 40, are also in the form an annular array extending from the distal end of the prosthetic device, from their connection points 41 with the conical section 35 of the metal base 30, to the clamping fingers 34a. Clamping fingers 34a are thus cooperable with clamping fingers 33a carried by its throat section 32 to clamp the device in the aortic orifice. Bracing elements 40 are configured so as to engage the inner surface of the aorta, preferably adjacent to, the distal end of the prosthetic device, in order to brace that end when the prosthetic device is implanted in the aortic annulus. It is of course critical that they be configured so as not to obstruct or occlude the coronary arteries adjacent to the aortic annulus (as brought out in the description below of FIG. 16f).

Bracing elements 40 may be made of the same material as the metal base 30, e.g., Nitinol. For simplification purposes, FIG. 11 omits the inner liner and the prosthetic valve, e.g. 11 and 16, respectively, FIG. 5

Figure 12:
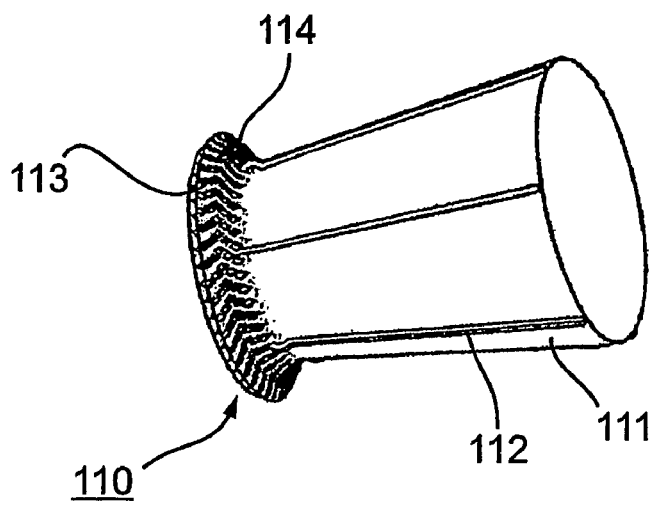
FIG. 12 is a three-dimensional view illustrating yet another prosthetic device constructed in accordance with the present invention.
Figure 13:
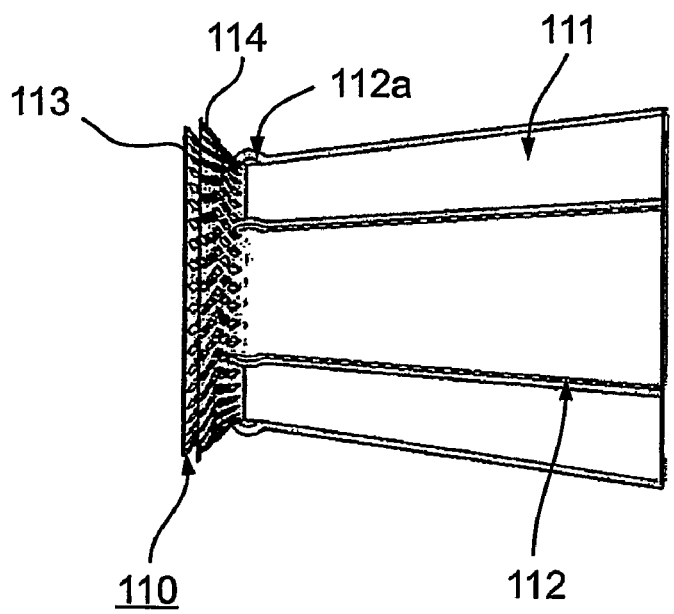
FIG. 13 is a side view of the device of FIG. 12.
Figure 14:
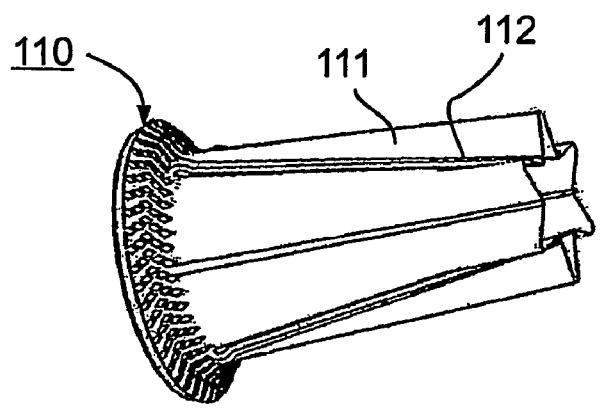
FIG. 14 illustrates the prosthetic device of FIGS. 12 and 13 in a mid-closed (not completely closed) condition.

The Prosthetic Device of FIGS. 12-14

FIGS. 12-14 illustrate a prosthetic device substantially different from that described above, in that the metal base occupies only the throat section (2, FIG. 2) of the prosthetic device mounted in the aortic annulus; that is, the metal base, designated 110 in FIGS. 12-14, does not extend to, or constitute a part of, the diverging conical section (5, FIG. 2) of the prosthetic device. The diverging conical section (5, FIG. 2) of the prosthetic device is occupied only by the envelope designated 111 in FIGS. 12-14, which plastic envelope also serves as a prosthetic valve. Thus, during systole, the envelope 111 opens and assumes the diverging conical configuration so as to produce the non-turbulent blood flow into the aorta with pressure recovery at the distal end of the envelope; whereas during diastole, envelope 111 collapses to block the flow therethrough.

Metal base 110, which corresponds only to the throat section (e.g., 12, FIG. 5) of the prosthetic device to be implanted into the aortic annulus, further includes two annular arrays of fingers 113, 114, on its opposite sides for engaging the opposite faces of the valve leaflets within the aortic annulus, and thus correspond to annular clamps 13, 14, of FIG. 5.

Envelope 111 lines the inner surface of metal base 110. It then extends outwardly of the metal base to define the diverging conical section of the prosthetic device, and also a prosthetic valve carried by the distal end of the prosthetic device (corresponding to sections 15 and valve 16, respectively, in FIG. 5).

Envelope 111 further includes a plurality of axially-extending struts 112 pivotally mounted at 112a to the metal base 110, to permit the envelope to expand, during systole, to its open-valve condition to permit blood therethrough, while at the same time assuming the diverging conical configuration for producing non-turbulent blood flow into the aorta with pressure recovery at the distal end. Struts 112 also permit envelope 111 to collapse during diastole in order to effectively block the blood flow therethrough, and thereby to perform the function of a prosthetic valve. FIG. 14 illustrates envelope 111 in a partially collapsed condition.

Reinforcing struts 112 may be of the same metal as metal base 110 and may be pivotally mounted to the base by integrally-formed hinges. Alternatively, reinforcing struts 112 may be of a different material, e.g., of a different metal or plastic, sufficiently stiff to support envelope 111 in its valve-open conical configuration during systole, and mechanically hinged to metal base 110 in any suitable manner.

It will thus be seen that the prosthetic device illustrated in FIGS. 12-14 not only acts to regulate the flow from the left ventricle into the aorta to produce the above-described non-turbulent flow into the aorta with pressure recovery, but also serves as a prosthetic valve which opens during systole and closes during diastole.

MODES OF DEPLOYMENT

As indicated above, the prosthetic device of the present invention is intended for implantation in an orifice formed in a wall of a body passageway. It is therefore constructed to have a compressed state for delivery via the body passageway to the implantation site and to be expandable at the implantation site to an expanded state for implantation in the orifice. The preferred embodiments of the invention described above are intended for implantation in the aortic annulus of a patient's heart, and therefore are constructed for transarterial delivery to the aortic annulus and expansion at the aortic annulus for implantation therein.

A single-sheath mode of deployment is described below with respect to FIGS. 15a-15h and 16a-16h; and a two-sheath mode of deployment is described below with respect to FIGS. 17a-17h.

Single-Sheath Mode of Deployment

FIGS. 15a-15h diagrammatically illustrate a method of deploying the prosthetic device, e.g., of FIG. 2, using a single sheath; whereas FIGS. 16a-16f illustrate that method used for deploying a prosthetic device of the construction illustrated in FIG. 11, i.e., including an annular array of bracing elements 40.

In the single-sheath method illustrated in FIGS. 15a-15h, the prosthetic device, generally designated PD and of the construction illustrated in FIG. 2, is to be implanted into the aortic orifice AO of the aortic valve AV by means of the annular clamps 3, 4. When so implanted, the throat section 2 of the prosthetic device is implanted in the aortic orifice AO, and the diverging conical section 5 of the prosthetic device is received within the aortic artery AA.

In order to deliver the prosthetic device PD to the implantation site, it is introduced into a catheter 200 including a balloon 201 and a sheath 202. Balloon 201, in its deflated condition, receives the throat section 2 and the two annular clamps 3, 4 of the prosthetic device. Sheath 202 encloses the complete prosthetic device and retains it including its annular clamps 13, 14 and diverging conical section 15, in a compressed state for transarterial delivery.

Figure 15A:
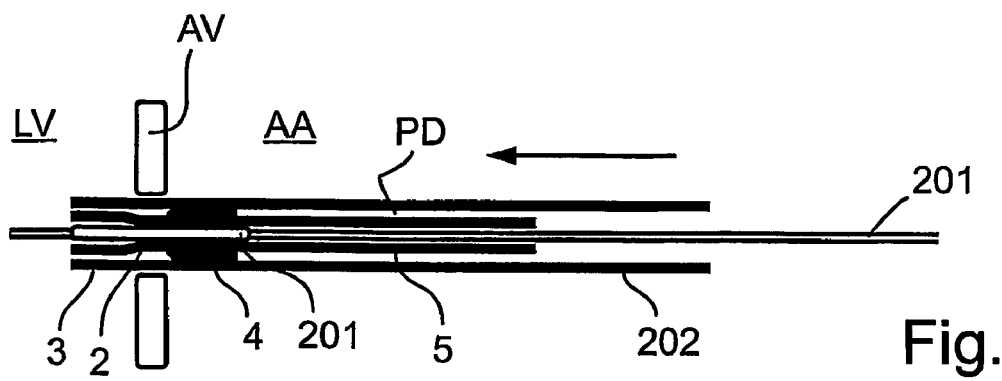
FIGS. 15a-15h and FIGS. 16a-16f illustrate a single-sheath method for implanting two types of prosthetic device in accordance with the present invention.
Figure 15B:
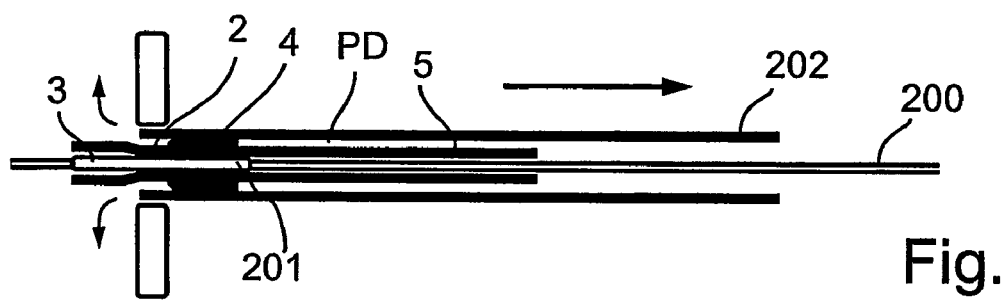
Figure 15C:
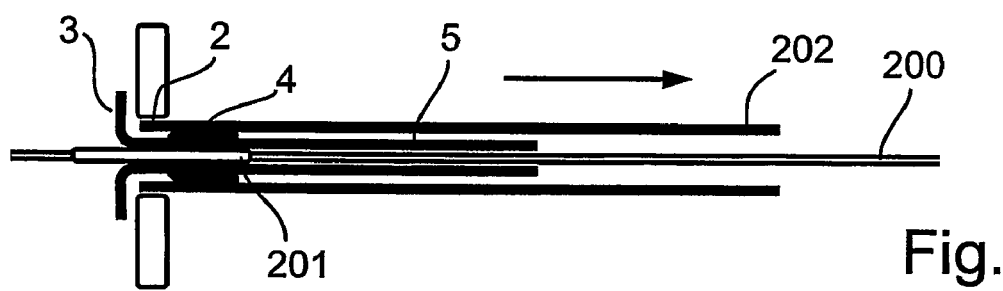
Figure 15D:
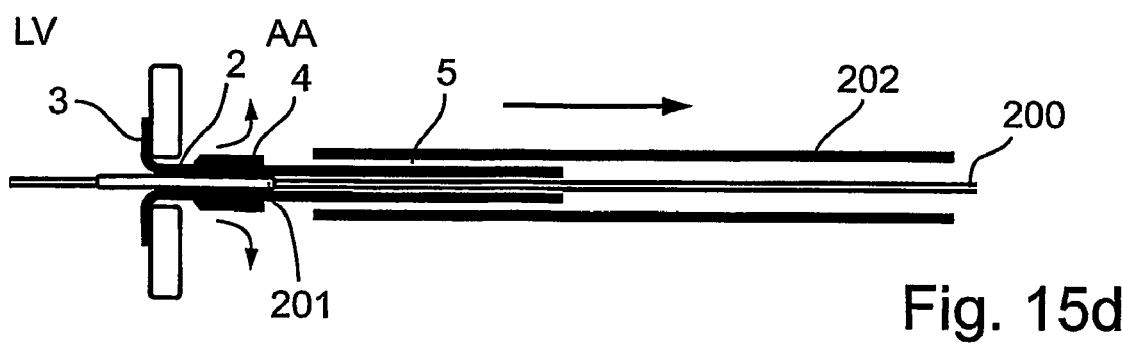
Figure 15E:
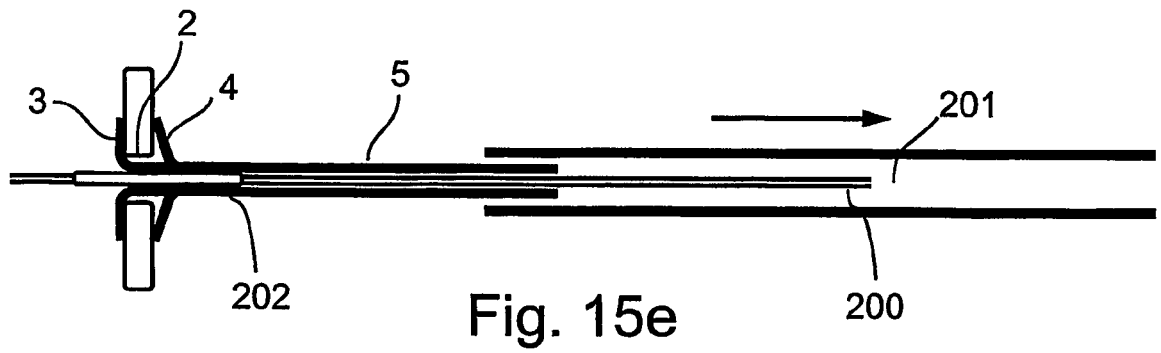

The catheter is introduced into a peripheral artery of the patient and manipulated in a conventional manner to bring the throat section 2 into alignment with the aortic orifice AO, with the two annular clamps 3, 4, located on opposite sides of the valve leaflets defining the orifice (FIG. 15a).

Figure 15F:
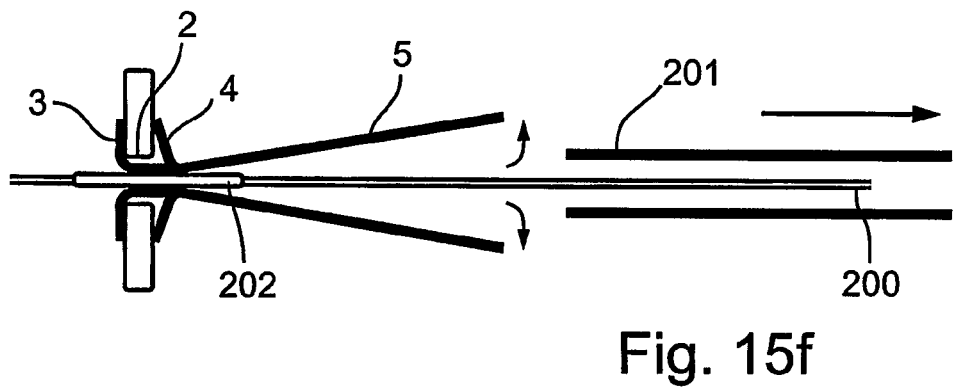
Figure 15G:
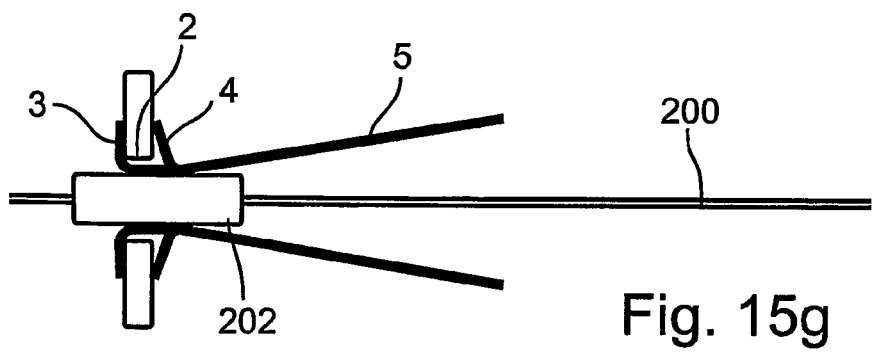
Figure 15H:
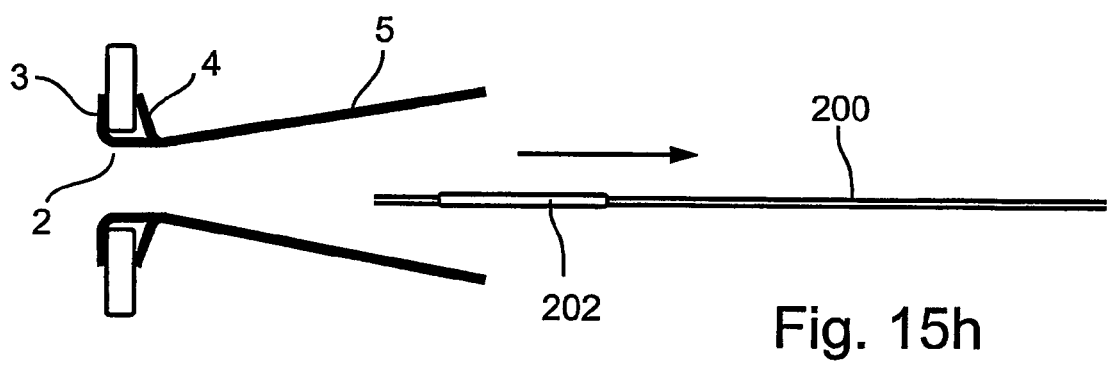

Sheath 202 is then moved to one side (FIG. 15b) to release, for expansion, first annular clamp 3 (FIG. 15c), then annular clamp 4 (FIGS. 15d, 15e), and finally the diverging conical section 5 of the prosthetic device (FIG. 15f). Balloon 201 is then inflated (FIG. 15g) to firmly press the base section 2 within the orifice, and then deflated (FIG. 15h) to permit the catheter 200, together with the balloon 201 and sheath 2902, to be removed from the artery, leaving the prosthetic device clamped within the orifice.

Since the prosthetic device is clamped with the orifice by the two annular clamps 3, 4, it may not be essential use a balloon; nonetheless this may be done to better assure proper implantation of the prosthetic device within the orifice. However, the provision of the two annular clamps 3, 4 enables the throat section 2 to be expanded only slightly, i.e., to a much lesser extent than in a conventional stent-type implantation, and thereby reduces the risk of obstructing or occluding the coronary arteries.

Figure 16A:
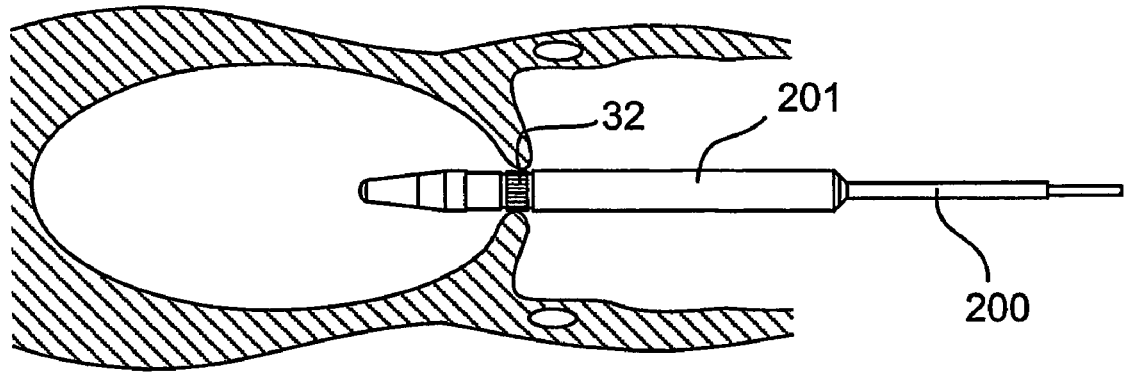
Figure 16B:
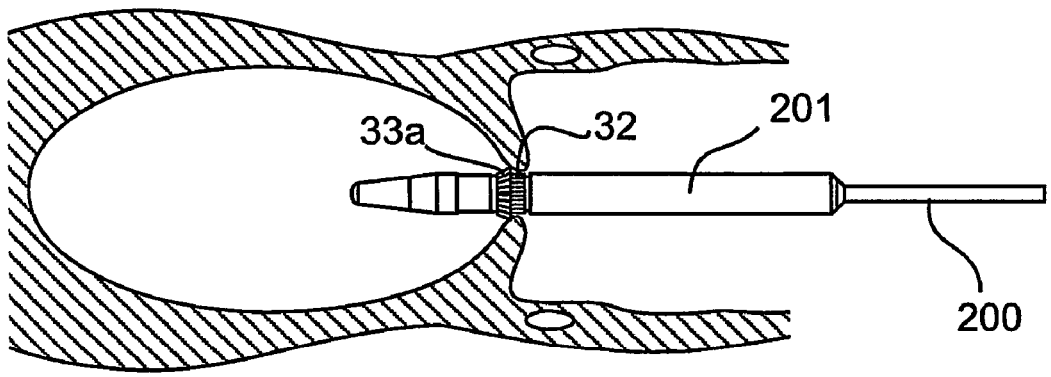
Figure 16C:
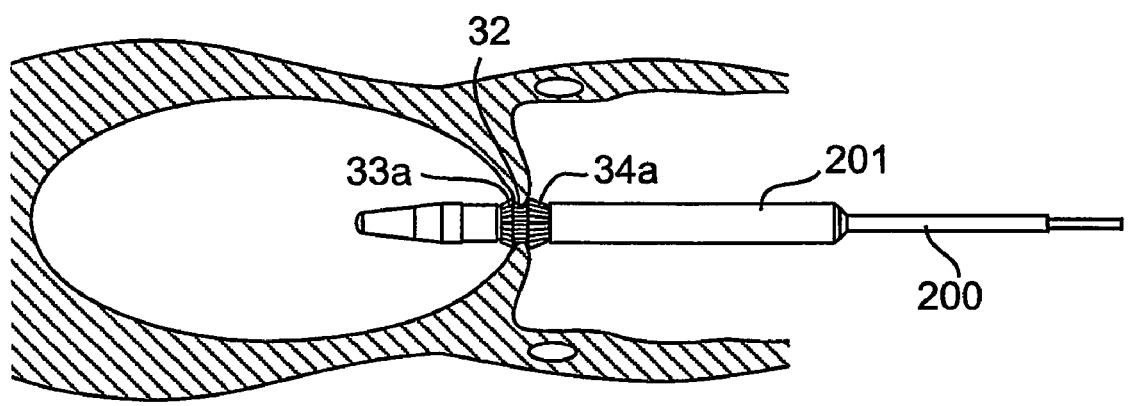
Figure 16D:
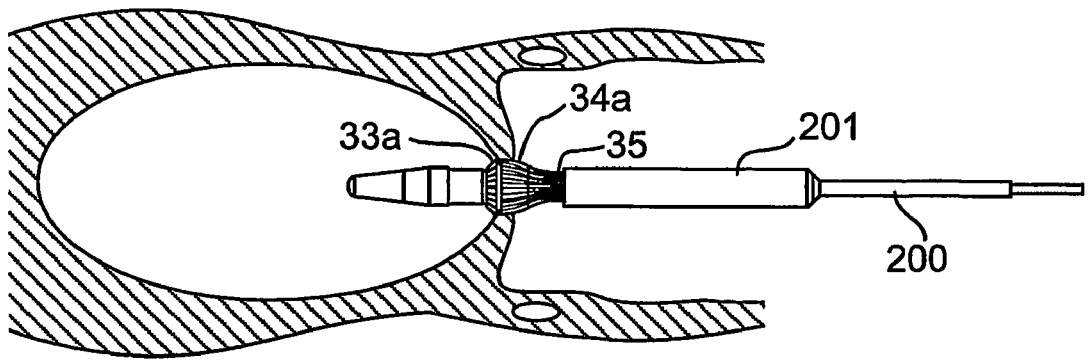
Figure 16E:
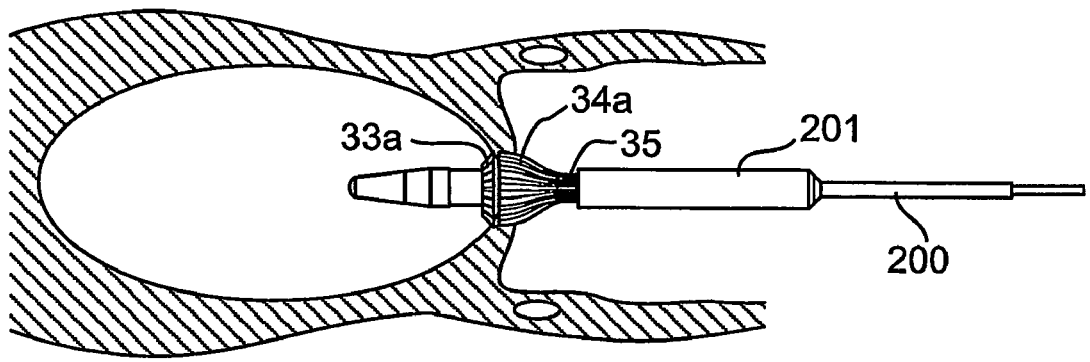
Figure 16F:
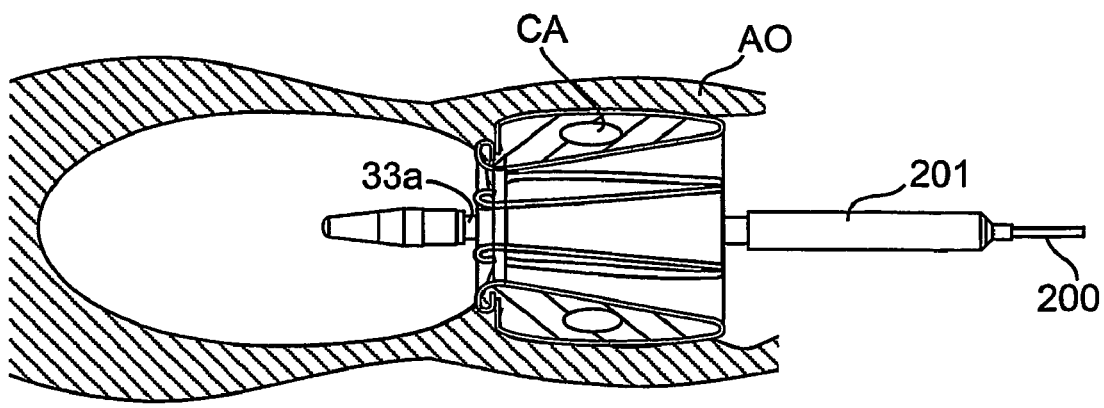

FIGS. 16a-16f illustrate the above-described one-sheath method of deploying the prosthetic device illustrated in FIG. 11 (i.e., including the annular array of bracing elements 40) through the following conditions: FIG. 16a, wherein the throat section 32 is located within the aortic orifice; FIG. 16b, wherein the sheath 201 has been moved to one side sufficient to release the fingers 33a of clamp 33; FIG. 16, wherein continued movement of the sheath releases the fingers 34a of the other annular clamp 34; FIGS. 16d and 16e, wherein continued movement of the sheath starts to release the diverging conical section 35 of the prosthetic device; and FIG. 16f, wherein the sheath has been moved sufficiently to release for expansion the complete prosthetic device, including the conical section 35 and the bracing elements 40 around the conical section. As shown particularly in FIG. 16f, the bracing elements 40 are configured so as not to obstruct the coronary arteries CA in the implanted condition of the prosthetic device.

While the method as illustrated in FIGS. 16a-16h does not use an inflatable balloon, it will be appreciated that such an inflatable balloon could also be used, as described above with respect to FIGS. 15a-15h, to better assure firm implantation of the prosthetic device in the aortic orifice.

Two-Sheath Mode of Deployment

FIGS. 17a-17h illustrate a two-sheath method of deployment of the prosthetic device. For purposes of example, this prosthetic device is that illustrated as FIGS. 4-8 described below.

Thus, in the two-sheath method, the catheter, therein designated 300, includes a first sheath 301 at the outer end to engage annular clamp 13 of the prosthetic device, and a second sheath 302 extending inwardly from sheath 301 so as to engage annular clamp 14 and the diverging conical section 15 of the prosthetic device. This is the condition illustrated in FIG. 17a.

Figure 17A:
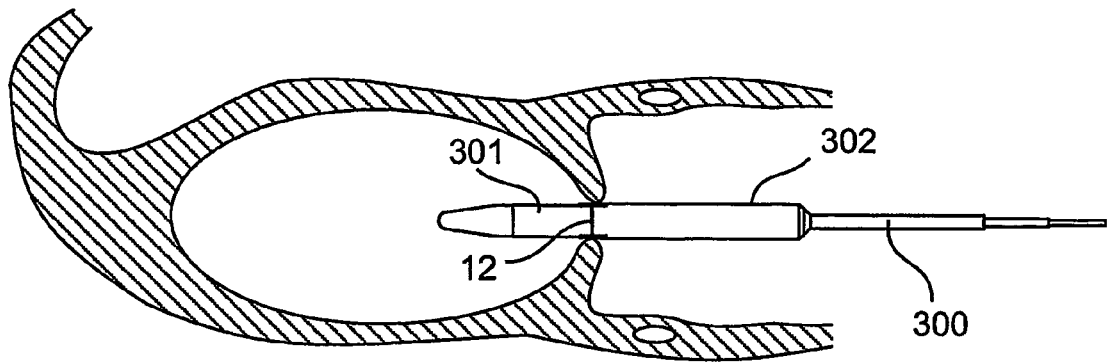
FIGS. 17a-17f illustrate a two-sheath method of implanting a prosthetic device in accordance with the present invention.
Figure 17B:
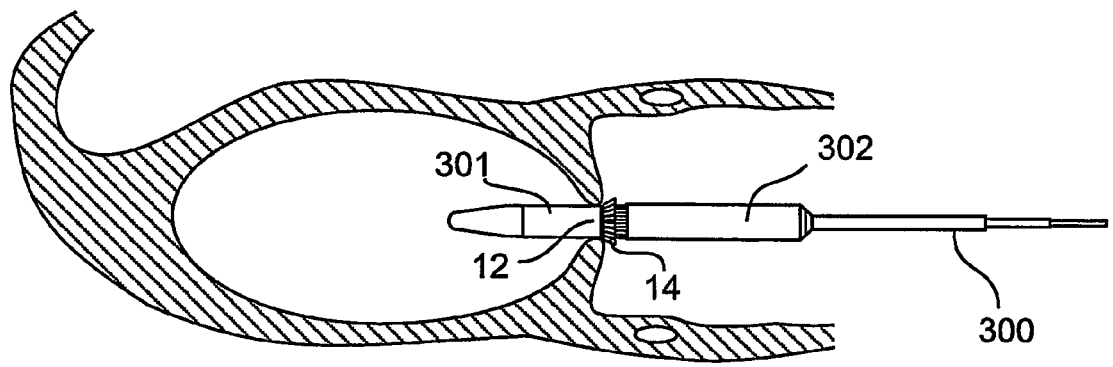
Figure 17C:
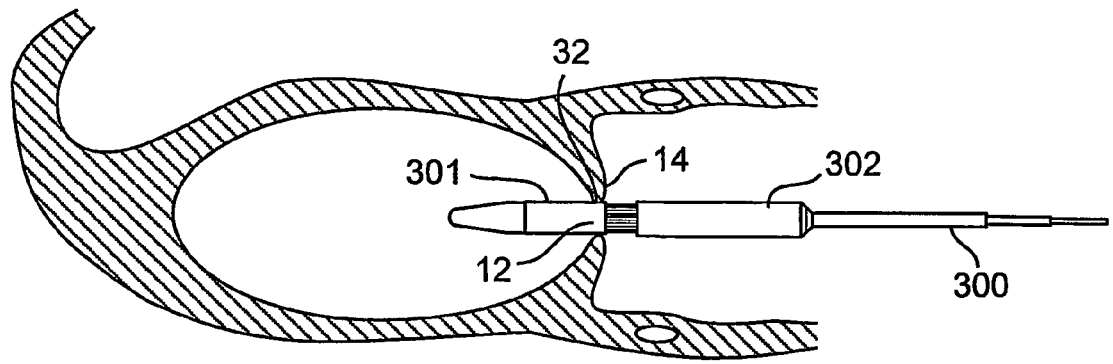

The catheter is first manipulated to locate throat section 12 of the prosthetic device in the aortic orifice (FIG. 17a). Sheath 302 is then moved laterally to one side (rightwardly) in order to release annular clamp 14 (FIG. 17b). When that clamp has been released, the catheter is then moved inwardly of the heart (leftwardly) a slight amount (FIG. 17c) to firmly bring clamping fingers 14a of annular clamp 14 against the respective face of the valve leaflets, such that annular clamp 14 firmly engages the aorta face (18, FIG. 8 of the valve leaflets as shown in FIG. 17c.

Figure 17D:
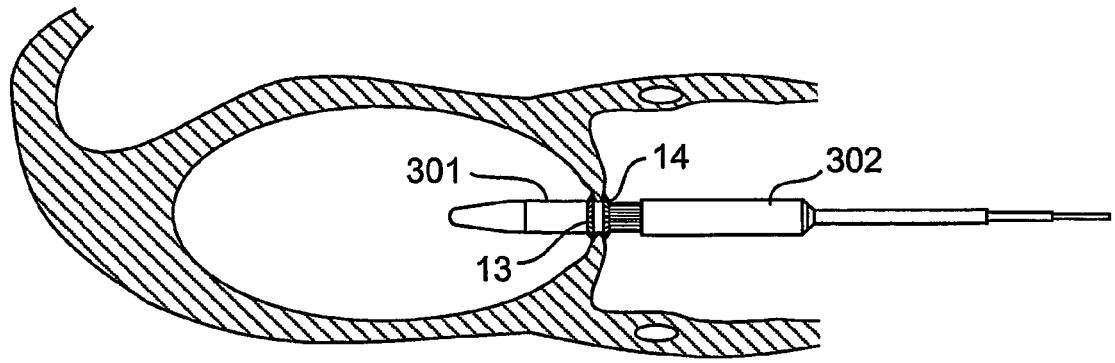

Outer sheath 301 is then moved away from sheath 302, i.e., leftwardly, further into the heart. This releases annular clamp 13 to its expanded state into contact with the surface (19, FIG. 8) of the valve leaflets facing the heart left-ventricle (FIG. 17d). At this time the catheter 300 may then be moved in the opposite direction (rightwardly) to firmly engage clamping fingers 13a of annular clamp 13 with that surface of the valve leaflet.

Figure 17E:
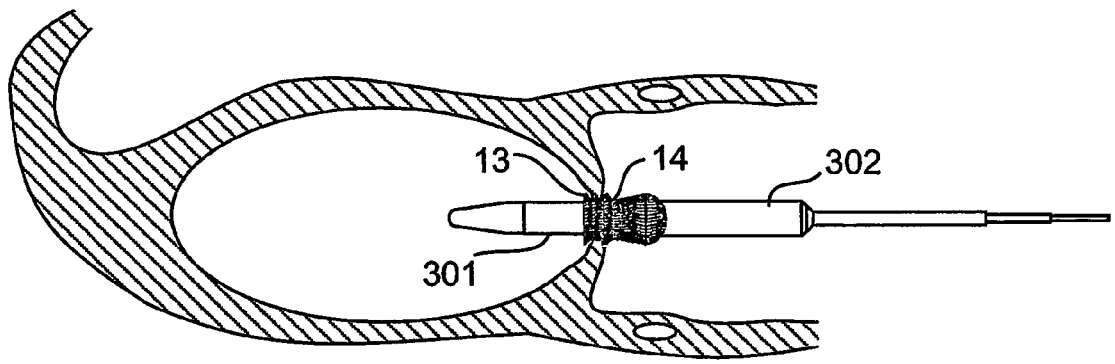
Figure 17F:
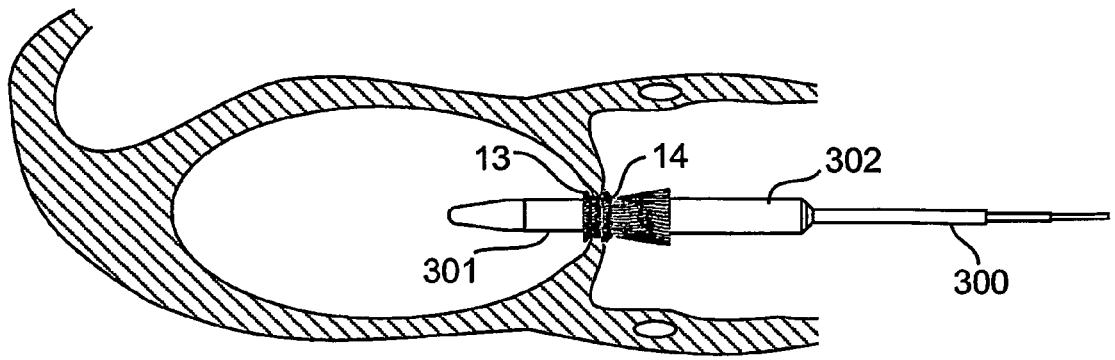

Sheath 302 within the aorta may then be moved further away from sheath 301, to thereby release the remainder of the prosthetic device for expansion, as shown in FIGS. 17e and 17f.

The catheter illustrated in FIGS. 17a-17f may also include a balloon (not shown) if desired, so as to slightly further expand the metal base 12 within the aortic orifice, in which case the balloon would then be deflated in order to permit removal of the catheter and its sheaths.

It will be appreciated that in the above described deployment methods, even if no balloon is used, the base section of the respective prosthetic device will still expand slightly when the respective sheath or sheaths are removed, to firmly seat the base section within the aortic annulus and also to permit removal of the catheter and its sheath or sheaths. However, providing such a balloon permits an additional expansion of the base section of the prosthetic device sufficient to better assure firm implantation within the orifice, but not to the extent of obstructing or occluding the coronary arteries.

While the invention has been described with respect to several preferred embodiments, it will be appreciated that these are set forth merely for purposes of example, and that many other variations, modifications and applications of the invention may be made.

What is claimed is:

1. A prosthetic device for use in the treatment of an aortic valve of a patient's heart, said prosthetic device having a compressed state for transarterial delivery and being expandable to an expanded state for implantation, said prosthetic device comprising:
an expandable support constructed so as to be implantable in the expanded state of the prosthetic device in an aortic annulus of the aortic valve;
an inner envelope having an upstream portion that lines the inner surface of the support, and a downstream portion which, when the prosthetic device is in the expanded state, is configured to extend into an aorta and defines a diverging conical section having a diameter that gradually increases from an upstream end of the diverging conical section to a downstream end of the section, which diverging conical section is configured to produce, during systole, a non-turbulent blood flow into the aorta with pressure recovery at the downstream end of the diverging conical section; and
a prosthetic valve coupled to the downstream portion of the envelope at the downstream end of the diverging conical section.

2. The prosthetic device according to claim 1, wherein, in the expanded state of the prosthetic device, said diverging conical section has an upstream end of 5-20 mm in diameter and a downstream end of 15-30 mm in diameter, and is of 15-45 mm in length.

3. The prosthetic device according to claim 2, wherein said upstream portion of the inner envelope includes a short straight section of uniform diameter within said aortic annulus effective to avoid flow separation through said upstream portion of the envelope.

4. The prosthetic device according to claim 3, wherein said short straight section has a length of 2-10 mm.

5. The prosthetic device according to claim 1, wherein said support includes two annular clamps engageable with the opposite sides of native leaflets of said aortic valve in the native leaflets' open positions for clamping the support to said leaflets.

6. The prosthetic device according to claim 5, wherein each of said two annular clamps includes an annular array of fingers.

7. The prosthetic device according to claim 6, wherein said support includes an annular array of bracing elements engageable with an inner surface of the aorta for bracing the prosthetic device within the aorta.

8. The prosthetic device according to claim 7, wherein said bracing elements are integrally formed at one end with said annular array of fingers of one of said annular clamps.

9. The prosthetic device according to claim 1, wherein said support, when the prosthetic device is in the expanded state extends to said downstream end of the diverging conical section, such that said inner envelope serves as a liner lining the inner surface of the support from said upstream end to said downstream end of the diverging conical section.

10. The prosthetic device according to claim 1, wherein said prosthetic valve comprises a plurality of leaflets movable to open and closed positions.

11. The prosthetic device according to claim 10, wherein said leaflets of the prosthetic valve are integral with said inner envelope.

12. The prosthetic device according to claim 1, wherein said diverging conical section of said inner envelope comprises a flexible pliable material.

13. The prosthetic device according to claim 1, wherein said diverging conical section of said inner envelope comprises a plurality of axially-extending reinforcing struts.

14. The prosthetic device according to claim 13, wherein said reinforcing struts are hingedly connected to said support.

15. The prosthetic device according to claim 1, wherein the support comprises a metal base.

* * * * *